United States Patent
Sugimoto

(10) Patent No.: US 10,472,308 B2
(45) Date of Patent: Nov. 12, 2019

(54) BUTENE CONVERSION METHOD AND MONOFLUOROBUTANE PURIFICATION METHOD

(71) Applicant: ZEON CORPORATION, Chiyoda-ku, Tokyo (JP)

(72) Inventor: Tatsuya Sugimoto, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 0 days.

(21) Appl. No.: 16/323,938

(22) PCT Filed: Aug. 17, 2017

(86) PCT No.: PCT/JP2017/029562
§ 371 (c)(1),
(2) Date: Feb. 7, 2019

(87) PCT Pub. No.: WO2018/037999
PCT Pub. Date: Mar. 1, 2018

(65) Prior Publication Data
US 2019/0177253 A1    Jun. 13, 2019

(30) Foreign Application Priority Data
Aug. 25, 2016   (JP) ................. 2016-165126

(51) Int. Cl.
| C07C 17/392 | (2006.01) |
| C07C 17/26  | (2006.01) |
| C07C 17/395 | (2006.01) |
| C07C 19/08  | (2006.01) |
| C07C 23/04  | (2006.01) |

(52) U.S. Cl.
CPC ............ *C07C 17/392* (2013.01); *C07C 17/26* (2013.01); *C07C 17/395* (2013.01); *C07C 19/08* (2013.01); *C07C 23/04* (2013.01)

(58) Field of Classification Search
CPC ..... C07C 17/395; C07C 17/02; C07C 17/383; C07C 19/08; C07C 17/03
See application file for complete search history.

(56) References Cited

U.S. PATENT DOCUMENTS

| 2,550,953    | A  | 5/1951  | Barrick         |
| 3,917,667    | A  | 11/1975 | Verbrugge et al.|
| 6,500,994    | B1 | 12/2002 | Brosch et al.   |
| 2011/0068086 | A1 | 3/2011  | Suzuki et al.   |
| 2016/0016869 | A1 | 1/2016  | Sugimoto        |
| 2016/0145177 | A1 | 5/2016  | Sugimoto        |

FOREIGN PATENT DOCUMENTS

| JP | S5062951 A    | 5/1975  |
| JP | S5946251 A    | 3/1984  |
| JP | S6032718 A    | 2/1985  |
| JP | 2002524431 A  | 8/2002  |
| JP | 2009292749 A  | 12/2009 |
| JP | 2013095669 A  | 5/2013  |
| JP | 2015044777 A  | 3/2015  |
| WO | 2009123038 A1 | 10/2009 |
| WO | 2014136877 A1 | 9/2014  |
| WO | 2015008781 A1 | 1/2015  |

OTHER PUBLICATIONS

Makosza et al., catalytic method for preparation of dichlorocyclopropane derivatives in aqueous medium,(Tetrahedron Letters 53 (1969) 4659-62).*
Sugimoto, method for purifying 2-fluorobutane, JP 2015044777 (A), Mar. 2015.*
George A. Olah et al., Synthetic Methods and Reactions. 63. Pyridinium Poly(hydrogen fluoride) (30% Pyridine-70% Hydrogen Fluoride): A Convenient Reagent for Organic Fluorination Reactions, The Journal of Organic Chemistry, Oct. 1979, pp. 3872-3881, vol. 44, No. 22.
Nov. 21, 2017, International Search Report issued in the International Patent Application No. PCT/JP2017/029562.
Takaoka Akio et al., F-Propene-Dialkylamine Reaction Products as Fluorinating Agents, Bulletin of the Chemical Society of Japan, Nov. 1979, pp. 3377-3380, vol. 52, No. 11.
W. Von E. Doering et al., The Addition of Dichlorocarbene to Olefins, Journal of the American Chemical Society, Dec. 1954, pp. 6162-6165, vol. 76, No. 23.
W. Von E. Doering et al., The Cis Addition of Dibromocarbene and Methylene to Cis- and Trans-Butene, Journal of the American Chemical Society, Oct. 1956, pp. 5447-5448, vol. 78, No. 20.
Feb. 26, 2019, International Preliminary Report on Patentability issued in the International Patent Application No. PCT/JP2017/029562.

* cited by examiner

*Primary Examiner* — Jafar F Parsa
(74) *Attorney, Agent, or Firm* — Kenja IP Law PC

(57) ABSTRACT

Provided is an industrially simple and cheap method for efficiently removing butene from crude monofluorobutane containing butene without causing substantial decomposition, transformation, or the like of the monofluorobutane. In a provided monofluorobutane purification method, crude monofluorobutane containing butene is brought into contact with trihalomethane in the presence of an alkali aqueous solution to convert the butene to a compound having a higher boiling point than the monofluorobutane, water is subsequently added to a reaction mixture obtained thereby to dissolve a produced salt, an organic layer is separated, and then the separated organic layer is purified by distillation.

4 Claims, No Drawings

BUTENE CONVERSION METHOD AND MONOFLUOROBUTANE PURIFICATION METHOD

TECHNICAL FIELD

The present disclosure relates to a butene conversion method and a monofluorobutane purification method. More specifically, the present disclosure relates to a method of converting butene in crude monofluorobutane and a method of purifying, using this conversion method, monofluorobutane that is useful as a plasma reaction gas (for example, an etching gas or chemical vapor deposition (CVD) gas) used in the field of manufacturing of semiconductor devices and the like, a fluorine-containing pharmaceutical intermediate, and a hydrofluorocarbon solvent. High-purity monofluorobutane, and particularly 2-fluorobutane, is suitable as a plasma etching gas, a CVD gas, or the like in the field of semiconductor device manufacturing using a plasma reaction.

BACKGROUND

Miniaturization in semiconductor manufacturing technology has been progressing in recent years with state-of-the-art processes now adopting line widths of 20 nm and even 10 nm. Since this miniaturization in the field of semiconductor manufacturing technology has been accompanied by increased technical difficulty in processing, techniques are being developed using various approaches in terms of used materials, equipment, processing methods, and so forth.

Against this background, the applicant has carried out diligent research in relation to dry etching gases that are also suitable for use in state-of-the-art dry etching processes. The applicant discovered that a saturated hydrofluorocarbon represented by $C_xH_yF_z$ (x represents 3, 4, or 5; y and z each represent a positive integer independently of one another; and y>z), such as 2-fluorobutane, has superior performance to monofluoromethane used in etching of silicon nitride films (PTL 1).

A number of conventional methods for producing 2-fluorobutane are known.

PTL 2 discloses that 2-fluorobutane was obtained with a yield of 46% by bringing N,N'-diethyl-3-oxo-methyltrifluoropropylamine (fluorinating agent) into contact with 2-butanol. PTL 3 describes bringing sulfur hexafluoride into contact with sec-butyllithium cyclohexane/hexane solution to obtain sec-butyl fluoride.

PTL 4 describes a method of producing 2-fluorobutane by bringing 2-butanol and a fluorine-containing ylide into contact in the presence of 2-butene. PTL 5 describes hydrogenating 2-fluorobutadiene in the presence of a catalyst to obtain 2-fluorobutane.

In PTL 6, high-purity 2-fluorobutane is obtained by performing distillation, drying, and denitrification/deoxygenation with respect to crude 2-fluorobutane obtained by a reaction step.

However, although methods for producing 2-fluorobutane are described in these conventional techniques, hardly any information is provided about the purity of the obtained 2-fluorobutane or impurities therein, and a method for efficiently purifying 2-fluorobutane is not described.

NPL 1 and 2 describe methods for obtaining a dihalopropane product through addition of dihalocarbene to an olefin. In the method described in NPL 1, cis-/trans-butene is reacted with bromoform and potassium t-butoxide to obtain a dibromocyclopropane product. In the method described in NPL 2, cyclohexene and isobutene are reacted with chloroform and potassium t-butoxide to obtain a dichlorocyclopropane product.

CITATION LIST

Patent Literature

PTL 1: WO 2009/123038 A1
PTL 2: JP S59-46251 A
PTL 3: JP 2009-292749 A
PTL 4: JP 2013-095669 A
PTL 5: Specification of U.S. Pat. No. 2,550,953
PTL 6: WO 2014/136877 A1
PTL 7: JP 2002-524431 A
PTL 8: WO 2015/8781 A1
PTL 9: JP 2015-44777 A

Non-Patent Literature

NPL 1: Journal of the American Chemical Society, Vol. 76, 6162 (1954)
NPL 2: Journal of the American Chemical Society, Vol. 78, 5447 (1956)

SUMMARY

Technical Problem

The inventor succeeded in obtaining high-purity 2-fluorobutane as described in PTL 6. However, from a viewpoint of industrial productivity, it would be beneficial to more efficiently remove butene present as a main impurity. Since separated butene is a gaseous substance at normal temperature, this places various restrictions on handling thereof in industry.

In view of the above, the inventor carried out diligent studies with the aim of achieving simple removal of the majority of butene contained in a crude product of 2-fluorobutane (hereinafter, also referred to as "crude 2-fluorobutane").

As one example of a method for removing an unsaturated impurity from crude fluorinated butane, PTL 7 describes a method of removing a fluorotrichloroethylene product contained in 1,1,1,3,3-pentafluorobutane through addition of a diatomic molecule such as hydrogen chloride, fluorine, chlorine, or hydrogen to the fluorotrichloroethylene product.

However, when this method was adopted in the purification of crude 2-fluorobutane, a problem of 2-fluorobutane decomposition (dehydrofluorination) occurred when a highly reactive reactant such as fluorine or chlorine was used.

On the other hand, if butene that is a by-product is hydrogenated using hydrogen having low reactivity, the gaseous substance butane is produced, and consequently the objective of efficient impurity removal cannot be achieved.

Therefore, the inventor developed "a method of bringing crude 2-fluorobutane containing butene into contact with a brominating agent that can form a bromonium ion and water or an alcohol having a carbon number of 4 or less in an aprotic polar solvent to convert the butene to a high-boiling point compound (PTL 8)" and "a method of, with respect to crude 2-fluorobutane containing butene, dimerizing the butene in an aliphatic hydrocarbon solvent in the presence of a Lewis acid catalyst such as aluminum chloride to convert the butene to a high-boiling point hydrocarbon compound (PTL 9)" as methods for reducing butene content.

However, the method described in PTL 8 suffers from a problem that the used brominating agent and aprotic polar solvent are comparatively expensive and production cost is high. Moreover, the method described in PTL 9 suffers from a problem that a halogen exchange reaction may occur through the action of aluminum chloride used as a Lewis acid, resulting in chlorination of the target 2-fluorobutane.

In view of the above, there has been demand for the development of an industrially simple and cheap method for reducing the amount of butene present as an impurity without causing substantial decomposition, transformation, or the like of the required monofluorobutane, such as 2-fluorobutane.

The present disclosure was completed under the circumstances set forth above and aims to provide a butene conversion method and monofluorobutane purification method for industrially simple and cheap reduction of butene content in crude monofluorobutane containing butene.

Solution to Problem

The inventor carried out diligent studies to solve the problem set forth above. As a result, the inventor discovered an industrially simple and cheap method that, by bringing crude monofluorobutane containing butene into contact with trihalomethane in the presence of an alkali aqueous solution, enables efficient reduction of content of the butene without causing substantial decomposition, transformation, or the like of the monofluorobutane in the crude monofluorobutane, and thereby completed the present disclosure.

Thus, the present disclosure provides the following conversion methods (1) to (4) and the following purification method (5).

(1) A conversion method comprising bringing crude monofluorobutane containing butene into contact with trihalomethane in the presence of an alkali aqueous solution to convert the butene to a compound having a higher boiling point than the monofluorobutane.

(2) The conversion method according to the foregoing (1), wherein the crude monofluorobutane contains the butene in a proportion of at least 5 mass % and not more than 50 mass %.

(3) The conversion method according to the foregoing (1) or (2), wherein the contact is performed in the presence of a phase transfer catalyst.

(4) The conversion method according to any one of the foregoing (1) to (3), wherein the alkali aqueous solution is an aqueous solution of an alkali metal hydroxide.

(5) A monofluorobutane purification method comprising converting butene to a compound having a higher boiling point than monofluorobutane by the conversion method according to any one of the foregoing (1) to (4), subsequently adding water to a reaction mixture obtained thereby to dissolve a produced salt, separating an organic layer, and purifying by distillation the organic layer that is separated.

Advantageous Effect

According to the present disclosure, it is possible to reduce butene content in crude monofluorobutane containing butene in an industrially simple and cheap manner, without causing substantial decomposition, transformation, or the like of the monofluorobutane.

Moreover, according to the present disclosure, is it possible to provide a method of purifying crude monofluorobutane containing butene in an industrially simple and cheap manner.

DETAILED DESCRIPTION

The following provides a detailed description of the present disclosure in sections relating to 1) a butene conversion method and 2) a crude monofluorobutane purification method.

1) Butene Conversion Method

A presently disclosed butene conversion method is a method of bringing crude monofluorobutane containing butene into contact with trihalomethane in the presence of an alkali aqueous solution to convert the butene to a compound having a higher boiling point than the monofluorobutane.

(1) Crude Monofluorobutane

The crude monofluorobutane used in the presently disclosed method contains butene as an impurity. Although no specific limitations are placed on the butene content, the butene content relative to the overall crude monofluorobutane is preferably 5 mass % or more, more preferably 10 mass % or more, and even more preferably 15 mass % or more, and is preferably 50 mass % or less, more preferably 40 mass % or less, and even more preferably 35 mass % or less.

Examples of the monofluorobutane include 2-fluorobutane (boiling point: 24° C. to 25° C.), 1-fluorobutane (boiling point: 32° C.), 1-fluoro-2-methylpropane (isobutyl fluoride) (boiling point: 21° C. to 22° C.), and 2-fluoro-2-methylpropane (t-butyl fluoride) (boiling point: 12° C. to 13° C.).

Of these examples, 2-fluorobutane is particularly industrially useful and is preferable as the monofluorobutane.

Examples of the butene contained in the crude monofluorobutane include 1-butene (boiling point: −6.3° C.), (E)-2-butene (boiling point: 0.9° C.), (Z)-2-butene (boiling point: 3.7° C.), and isobutene (boiling point: −6.9° C.).

Note that the boiling point of the butene contained in the crude monofluorobutane is normally lower than the boiling point of the monofluorobutane.

Crude 2-fluorobutane, for example, typically contains 1-butene, (E)-2-butene, and (Z)-2-butene as butenes.

Crude 2-fluorobutane containing such butenes can be obtained by causing a fluorinating agent to act on 2-butanol. For example, a method in which a poly(hydrogen fluoride) complex of pyridine is used as a fluorinating agent is described in Journal of Organic Chemistry, Vol. 44, 3872 (1979). Moreover, a method in which N,N'-diethylaminohexafluoropropane prepared from hexafluoropropene and diethylamine is used as a fluorinating agent is described in Bulletin of the Chemical Society of Japan, Vol. 52, 3377 (1979).

Crude 2-fluorobutane can also be obtained by a method in which 2-bromobutane or 2-(alkylsulfonyloxy)butane is treated with an alkali metal fluoride such as potassium fluoride or cesium fluoride.

In another example, crude isobutyl fluoride typically contains isobutene as a butene.

Crude isobutyl fluoride containing isobutene can be obtained by, for example, reacting isobutyl alcohol with chlorotrimethylsilane in the presence of pyridine to convert the isobutyl alcohol to 1-trimethyl siloxy-2-methylpropane, and then bringing the 1-trimethylsiloxy-2-methylpropane into contact with diethylaminosulfur trifluoride serving as a fluorinating agent (JP S60-32718 A). In this situation, t-butyl fluoride obtained as a rearrangement product is contained in the reaction product in a molar ratio of isobutyl fluoride and t-butyl fluoride of 95:5 (isobutyl fluoride:t-butyl fluoride).

(2) Trihalomethane

Examples of the trihalomethane used in the presently disclosed method include chloroform, bromodichloromethane, dichloroiodomethane, dibromochloromethane, bromochloroiodomethane, chlorodiiodomethane, bromoform, dibromoiodomethane, and iodoform. Of these examples, chloroform, bromodichloromethane, and bromoform are preferable due to their high boiling points and ease of acquisition.

The amount of the trihalomethane that is used is preferably at least an equivalent (molar equivalent) of the butene contained in the crude monofluorobutane, and is more preferably 2 equivalents or more since the trihalomethane can also be used as a reaction solvent. Specifically, a rough guide for the amount of the trihalomethane is at least 0.5 mL and not more than 2 mL, and preferably at least 0.8 mL and not more than 1.2 mL per 1 g of the crude monofluorobutane. The use of a small amount of the trihalomethane is undesirable because the amount of the subsequently described dihalocarbene that is produced and addition reaction to the butene become insufficient, and a large amount of the butene remains. Conversely, the use of an excessive amount of the trihalomethane is financially disadvantageous.

(3) Alkali Aqueous Solution

The presently disclosed conversion method is carried out in the presence of an alkali aqueous solution.

The alkali that is used is preferably an alkali metal hydroxide. Examples of alkali metal hydroxides that may be used include lithium hydroxide, sodium hydroxide, potassium hydroxide, and cesium hydroxide. Of these examples, sodium hydroxide and potassium hydroxide are more preferable due to their high solubility in water and ease of concentration adjustment.

The amount of the alkali that is used is preferably at least an equivalent (molar equivalent) relative to the butene in the crude monofluorobutane, and is more preferably at least 2 equivalents and not more than 5 equivalents. If too little alkali is used, production efficiency of the subsequently described dihalocarbene deteriorates, and the reaction becomes time consuming. Conversely, the use of too much alkali is undesirable because the amount of the alkali aqueous solution that is used increases, and the amount of waste water increases.

The concentration of the alkali aqueous solution is preferably 30 mass % or more, and more preferably 50 mass % or more, and is preferably 80 mass % or less, and more preferably 75 mass % or less. If the concentration of the alkali aqueous solution is low, production efficiency of the subsequently described dihalocarbene deteriorates, and the reaction becomes time consuming. Conversely, if the concentration of the alkali aqueous solution is too high, the reaction occurs suddenly. This is dangerous and may cause problems such as contents spurting out of the reaction vessel.

(4) Phase Transfer Catalyst

In the presently disclosed method, it is preferable that a phase transfer catalyst is added into the reaction system in order to promote the reaction. The phase transfer catalyst may be any phase transfer catalyst that is typically used in synthesis reactions without any specific limitations. Examples of phase transfer catalysts that may be used include polyethers, amino alcohols, and quaternary salts. Of these examples, quaternary salts are preferable because the effects of the presently disclosed method can easily be obtained.

Examples of polyethers include crown ethers such as 15-crown-5, 18-crown-6, dibenzo-18-crown-6, dibenzo-24-crown-8, and dicyclohexyl-18-crown-6; and polyoxyalkylene glycols such as polyethylene glycol, polypropylene glycol, and polyethylene glycol monomethyl ether.

Examples of amino alcohols include tris[2-(2-methoxyethoxy)ethyl]amine and cryptates.

The quaternary salt is composed of a cation (positive ion) produced through bonding of four carbon-containing substituents to a heteroatom, such as a nitrogen atom or a phosphorus atom, and a counter anion (negative ion).

The heteroatom may be any atom from group VB of the periodic table without any specific limitations, and is preferably a nitrogen atom or a phosphorus atom.

Although no specific limitations are placed on the carbon number of the carbon-containing substituents, the carbon number is normally 1 to 30, and more preferably 1 to 20. The carbon-containing substituents are not specifically limited so long as they each include a carbon that is directly bonded to the heteroatom, and examples thereof include alkyl groups, aryl groups, aralkyl groups, alkenyl groups, and alkynyl groups.

These carbon-containing substituents may include a substituent that does not affect the reaction such as an alkoxy group, a halogen atom, or an alkylthio group. Moreover, the carbon-containing substituents may include a divalent group that does not affect the reaction such as a carbonyl group, a sulfonyl group, or a sulfinyl group in the structure thereof.

Furthermore, a plurality of carbon-containing substituents in the quaternary salt may be bonded to one another as a ring with a nitrogen atom to form a pyridinium group or a picolinium group.

Note that the four carbon-containing substituents may be the same as or different from one another.

Of these examples, alkyl groups such as a methyl group, an ethyl group, a propyl group, a butyl group, an octyl group, a lauryl group, and a hexadecyl group; optionally substituted aryl groups such as a phenyl group, a 2-methylphenyl group, a 4-methylphenyl group, a 4-ethylphenyl group, and a naphthyl group; and optionally substituted aralkyl groups such as a benzyl group, a 2-methylbenzyl group, a 4-methylbenzyl group, a 2-methoxybenzyl group, and a 4-methoxybenzyl group are preferable as the carbon-containing substituents.

Examples of the counter anion (negative ion) include a halide ion, a hydroxide ion, a hydrogen sulfate ion, and a phosphate ion. Of these examples, a halide ion is preferable because the effects of the presently disclosed method can easily be obtained.

The halide ion may, for example, be a chloride ion, a bromide ion, a fluoride ion, or an iodide ion, and is preferably a chloride ion or a bromide ion.

Specific examples of quaternary salts include quaternary ammonium halides, quaternary phosphonium halides, quaternary ammonium hydroxides, quaternary phosphonium hydroxides, quaternary ammonium hydrogen sulfates, and quaternary phosphonium hydrogen sulfates. Tetrabutylammonium sulfate or the like may also be used as the quaternary salt.

Of these examples, quaternary ammonium halides and quaternary phosphonium halides are preferable, and quaternary phosphonium halides are more preferable.

Examples of quaternary ammonium halides include tetramethylammonium bromide, tetramethylammonium chloride, tetraethylammonium bromide, tetrapropylammonium bromide, tetrabutylammonium bromide, tetrabutylammonium chloride, cetyltrimethylammonium bromide, benzyltriethyl ammonium chloride, trimethylbenzylammonium bromide, and trioctylmethylammonium chloride.

Examples of quaternary phosphonium halides include tetrabutylphosphonium bromide, tetrabutylphosphonium chloride, benzyltriphenylphosphonium chloride, benzyltriphenylphosphonium bromide, butyltriphenylphosphonium bromide, and tetraphenylphosphonium bromide.

These phase transfer catalysts may be used individually or as a combination of two or more types.

The amount of the phase transfer catalyst that is used may be selected as appropriate depending on the reaction conditions. Specifically, the amount of the phase transfer catalyst that is used relative to the butene (100 mol %) contained in the crude monofluorobutane is normally within a range of 0.001 mol % to 20 mol %, is preferably 0.01 mol % or more, and more preferably 0.1 mol % or more, and is preferably 10 mol % or less, and more preferably 5 mol % or less.

(5) Conversion Method

The presently disclosed conversion method is a method of bringing crude monofluorobutane containing butene into contact with trihalomethane in the presence of an alkali aqueous solution to convert the butene to a compound having a higher boiling point than the monofluorobutane. The reaction mechanism in the presently disclosed conversion method is thought to be as follows.

First, dihalocarbene is produced through reaction of the trihalomethane and the alkali. For example, dichlorocarbene is produced in a case in which the trihalomethane is chloroform.

Next, the produced dihalocarbene undergoes addition at a double bond of the butene to convert the butene to a compound with a dihalocyclopropane ring skeleton that has a higher boiling point than the monofluorobutane.

Reactions in which 1-butene, 2-butene, or isobutene as the butene reacts with the dihalocarbene to yield a compound with a dihalocyclopropane ring skeleton (compound having a carbon number of 5) are indicated in the following formulae.

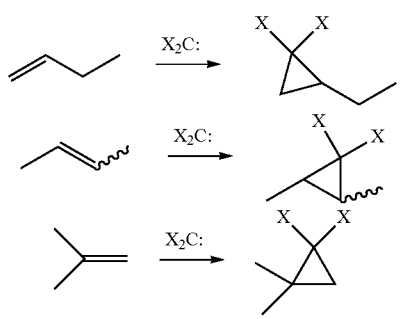

(In the formulae, X represents a halogen atom and a wavy line indicates a cis isomer and/or trans isomer.)

Although no specific limitations are placed on embodiments of the presently disclosed conversion method, in one example, an alkali aqueous solution is first charged to a reaction vessel or an alkali and water are charged to a reaction vessel to prepare an alkali aqueous solution, and then the reaction vessel is cooled to a freely selected temperature. Butene-containing crude monofluorobutane, trihalomethane, and, as desired, a phase transfer catalyst are then charged to the reaction vessel, and the contents of the reaction vessel are stirred. This stirring is preferably performed vigorously to an extent that an interface between the organic layer and the aqueous layer becomes unidentifiable.

Progress of the reaction may be tracked by gas chromatography, for example, and further alkali aqueous solution may be added if residual butene is present.

The reaction temperature is preferably within a range of $-30°$ C. to $70°$ C., and more preferably within a range of $0°$ C. to $50°$ C. An excessively low reaction temperature is undesirable because solidification of the alkali aqueous solution itself may occur, the rate of reaction may slow, and completion of the reaction may become time consuming. Conversely, an excessively high reaction temperature is undesirable because the monofluorobutane itself becomes readily volatilizable, and the amount of the target monofluorobutane may decrease.

The reaction time is normally at least 0.5 hours and not more than 20 hours, and preferably at least 1 hour and not more than 10 hours, but is dependent on the type of alkali that is used, the concentration of the alkali, and the reaction temperature. An excessively short reaction time is undesirable because the reaction is not complete and a large amount of the butene may remain. Conversely, an excessively long reaction time is undesirable because the amount of the target monofluorobutane may decrease due to the monofluorobutane itself being a readily volatilizable compound.

Through the presently disclosed conversion method, the butene contained in the crude monofluorobutane is converted to a compound with a dihalocyclopropane ring skeleton that has a higher boiling point than the monofluorobutane. Consequently, high-purity monofluorobutane with low butene content can be obtained in a simple manner through distillation of an obtained organic layer as subsequently described.

2) Purification Method

A presently disclosed monofluorobutane purification method is a method of obtaining high-purity monofluorobutane from crude monofluorobutane containing butene. The presently disclosed monofluorobutane purification method includes converting butene to a compound having a higher boiling point than monofluorobutane by the presently disclosed conversion method, subsequently adding water to the obtained reaction mixture to dissolve a produced salt, and then separating the organic layer and purifying the separated organic layer by distillation.

In the presently disclosed conversion method, a salt (for example, an alkali metal halide such as sodium chloride or potassium chloride) derived from the alkali and the trihalomethane used in the reaction is produced and precipitates. Water is added to the obtained reaction mixture in order to dissolve the precipitated salt (for example, an alkali metal halide), and the reaction mixture separates into an organic layer and an aqueous layer.

Thereafter, the organic layer is collected to recover post-conversion crude monofluorobutane containing trihalomethane, a compound with a dihalocyclopropane ring skeleton that is produced through conversion of the butene, and other impurities (hereinafter, this crude monofluorobutane is also referred to simply as "post-conversion crude monofluorobutane").

The recovered post-conversion crude monofluorobutane is further purified by distillation to remove impurities such as the trihalomethane and the compound with a dihalocyclopropane ring skeleton. The trihalomethane and the compound with a dihalocyclopropane ring skeleton can easily be removed by distillation since they normally have higher boiling points than the monofluorobutane.

The pressure during distillation is usually from normal pressure to $1 \times 10^6$ Pa, and preferably from normal pressure to $5 \times 10^5$ Pa.

A ratio of the reflux rate and the withdrawal rate in the distillation (hereinafter, also referred to as the "reflux ratio") is preferably set as 30:1 or more, and more preferably 40:1 or more in order to efficiently separate butene that readily adopts a gaseous state. If the reflux ratio is too small, the improvement in monofluorobutane purity is small because the butene is not efficiently separated, and the amount of monofluorobutane that can actually be collected for use as a product decreases because the size of the first fraction increases. Conversely, if the reflux ratio is too large, the distillation becomes time consuming because the time required until recovery per one withdrawal increases.

The distillation may be carried out by a batch process in a case in which a small amount of material is to be processed and may be carried out by a continuous process via a plurality of rectifying columns in a case in which a large amount of material is to be processed.

EXAMPLES

The following provides a more detailed description of the present disclosure through examples. However, the scope of the present disclosure is not limited by the following examples. Note that "%" indicates "mass %" unless otherwise specified.

Analysis conditions adopted in the following examples were as shown below.

<Gas Chromatography Analysis (GC Analysis)>
  Apparatus: HP-6890 (produced by Agilent Technologies)
  Column: InertCap-1 (produced by GL Sciences Inc.; length: 60 m, internal diameter: 0.25 mm, film thickness: 1.5 μm)
  Column temperature: Held at 40° C. for 10 minutes, raised at 20° C./min, and then held at 40° C. for 10 minutes
  Injection temperature: 200° C.
  Carrier gas: Nitrogen
  Split ratio: 100/1
  Detector: FID

Production Example 1

A 1 L glass reaction vessel equipped with a stirrer, a dropping funnel, and a collection trap was charged with 86 g of spray-dried potassium fluoride (produced by Sigma-Aldrich) and 400 mL of polyethylene glycol 400. Nitrogen was introduced into the reaction vessel from an outlet tube of the collection trap to provide a nitrogen atmosphere inside the reaction vessel. The reaction vessel was immersed in an oil bath and was heated to 70° C. Next, 135 g of 2-(p-toluenesulfonyloxy)butane that had been charged to the dropping funnel was added dropwise into the reaction vessel over 1.2 hours. After completion of this addition, the entire contents of the reaction vessel were further stirred for 7.5 hours at 70° C. Produced volatile components were collected in the collection trap, which was immersed in a dry ice/ethanol bath. Thereafter, the temperature of the oil bath was raised to 80° C., and two glass traps immersed in a dry ice/ethanol bath were connected to the reaction vessel in series. In addition, a pressure controller and a vacuum pump were connected to an outlet of the glass traps. The vacuum pump was operated, the pressure in the system was lowered stepwise to 50 kPa to 45 kPa, followed by 35 kPa to 30 kPa, and then 30 kPa to 25 kPa using the pressure controller, and volatile components were recovered in the glass traps.

The contents of the initial collection trap and the two glass traps were combined and then analyzed by gas chromatography. The mixture (37 g) was found to contain 2.71 area % of 1-butene, 12.61 area % of (E)-2-butene, 10.97 area % of (Z)-2-butene, and 73.71 area % of 2-fluorobutane.

Production Example 2

A 1 L glass reaction vessel equipped with a stirrer, a dropping funnel, and a collection trap was charged with 86 g of spray-dried potassium fluoride (produced by Sigma-Aldrich) and 400 mL of diethylene glycol. Nitrogen was introduced into the reaction vessel from an outlet tube of the collection trap to provide a nitrogen atmosphere inside the reaction vessel. The reaction vessel was immersed in an oil bath and was heated to 90° C. Next, 135 g of 2-(p-toluenesulfonyloxy)butane that had been charged to the dropping funnel was added dropwise into the reaction vessel over 2.5 hours. After completion of this addition, the entire contents of the reaction vessel were further stirred for 5 hours at 90° C. Produced volatile components were collected in the collection trap, which was immersed in a dry ice/ethanol bath. Thereafter, the temperature of the oil bath was lowered to 80° C., and two glass traps immersed in a dry ice/ethanol bath were connected to the reaction vessel in series. In addition, a pressure controller and a vacuum pump were connected to an outlet of the glass traps. The vacuum pump was operated, the pressure in the system was lowered stepwise to 50 kPa to 45 kPa, followed by 35 kPa to 30 kPa, and then 30 kPa to 25 kPa using the pressure controller, and volatile components were recovered in the glass traps.

The contents of the initial collection trap and the two glass traps were combined and then analyzed by gas chromatography. The mixture (22 g) was found to contain 4.13 area % of 1-butene, 19.80 area % of (E)-2-butene, 17.23 area % of (Z)-2-butene, and 58.84 area % of 2-fluorobutane.

Production Example 3

A 1 L glass reaction vessel equipped with a stirrer, a dropping funnel, a fraction collection receiver, and a Dimroth condenser was charged with 116 g of spray-dried potassium fluoride (produced by Sigma-Aldrich) and 800 mL of diethylene glycol. A nitrogen atmosphere was provided in the glass reaction vessel. The reaction vessel was immersed in an oil bath and was heated to 95° C. Thereafter, 152 g of methanesulfonyloxyisobutane was added into the reaction vessel over approximately 3.5 hours from the dropping funnel. After this addition, stirring was continued for 4 hours at 95° C., and produced low-boiling point product was collected in the fraction collection receiver, which was immersed in a dry ice/ethanol bath. Thereafter, the temperature of the oil bath was lowered to 80° C., and two glass traps immersed in a dry ice/ethanol bath were connected to the reaction vessel in series. In addition, a pressure controller and a vacuum pump were connected to an outlet of the glass traps. The vacuum pump was operated, the pressure in the system was lowered stepwise to 50 kPa to 45 kPa, followed by 35 kPa to 30 kPa, and then 30 kPa to 25 kPa using the pressure controller, and volatile components were recovered in the glass traps.

The contents of the fraction collection receiver and the two glass traps were combined and then analyzed by gas chromatography. The mixture (49 g) was found to contain 11.85 area % of isobutene, 79.69 area % of isobutyl fluoride, 7.32 area % of diisopropyl ether, and 1.14 area % of high-boiling point components. When this mixture was distilled using a simple distillation apparatus equipped with a short column, 41 g of a mixture containing 14.02 area % of isobutene and 85.36 area % of isobutyl fluoride was obtained.

Example 1

A 100 mL glass reaction vessel equipped with a stirrer and a Dimroth condenser (0° C. coolant circulated in condenser) was charged with 6.6 g of potassium hydroxide (purity: 85%; produced by Wako Pure Chemical Industries, Ltd.; same applies below) and was cooled to 0° C. The reaction vessel was further charged with 4.6 g of water to dissolve the potassium hydroxide. Next, 10 mL of chloroform was added as trihalomethane. In addition, 10.1 g of the mixture obtained in Production Example 1 (crude 2-fluorobutane containing butenes) and 0.13 g of benzyltriethylammonium chloride as a phase transfer catalyst were added. The organic layer was analyzed by gas chromatography at this point and was found to contain 2.24 area % of 1-butene, 10.64 area % of (E)-2-butene, 9.25 area % of (Z)-2-butene, 64.75 area % of 2-fluorobutane, and 12.99 area % of chloroform.

The contents of the reaction vessel were vigorously stirred for 30 minutes at 0° C. and were further stirred for 8 hours at room temperature (25° C.; same applies below). Thereafter, the stirring was stopped, the contents were allowed to settle, and the organic layer was reanalyzed by gas chromatography. In this analysis, 0.95 area % of 1-butene, 0.15 area % of (E)-2-butene, 0.04 area % of (Z)-2-butene, 61.25 area % of 2-fluorobutane, and 8.00 area % of chloroform were detected, and production of 29.54 area % of dichlorocyclopropane derivative (dichlorocarbene adduct) was confirmed in a high retention time region (time zone even later than time at which chloroform is detected).

Example 2

Operations were carried out in the same way as in Example 1 with the exception that, in Example 1, 0.13 g of benzyltriethylammonium chloride was changed to 0.34 g of tetrabutylammonium sulfate. When stirring was stopped, the contents were allowed to settle, and the organic layer was analyzed by gas chromatography, 1.30 area % of 1-butene, 3.62 area % of (E)-2-butene, 2.59 area % of (Z)-2-butene, 64.55 area % of 2-fluorobutane, and 13.01 area % of chloroform were detected, and production of 14.71 area % of dichlorocyclopropane derivative was confirmed in a high retention time region.

Example 3

Operations were carried out in the same way as in Example 1 with the exception that, in Example 1, 0.13 g of benzyltriethylammonium chloride was changed to 0.19 g of tetrabutylammonium bromide. When stirring was stopped, the contents were allowed to settle, and the organic layer was analyzed by gas chromatography, 1.18 area % of 1-butene, 3.68 area % of (E)-2-butene, 2.75 area % of (Z)-2-butene, 66.46 area % of 2-fluorobutane, and 12.72 area % of chloroform were detected, and production of 13.09 area % of dichlorocyclopropane derivative was confirmed in a high retention time region.

Example 4

Operations were carried out in the same way as in Example 1 with the exception that, in Example 1, 0.13 g of benzyltriethylammonium chloride was changed to 0.21 g of tetraphenylphosphonium bromide. When stirring was stopped, the contents were allowed to settle, and the organic layer was analyzed by gas chromatography, 0.90 area % of 1-butene, 1.27 area % of (E)-2-butene, 0.83 area % of (Z)-2-butene, 58.40 area % of 2-fluorobutane, and 12.86 area % of chloroform were detected, and production of 25.61 area % of dichlorocyclopropane derivative was confirmed in a high retention time region.

Example 5

Operations were carried out in the same way as in Example 1 with the exception that, in Example 1, 0.13 g of benzyltriethylammonium chloride was changed to 0.17 g of tetrabutylphosphonium bromide. When stirring was stopped, the contents were allowed to settle, and the organic layer was analyzed by gas chromatography, 1.08 area % of 1-butene, 0.90 area % of (E)-2-butene, 0.50 area % of (Z)-2-butene, 60.03 area % of 2-fluorobutane, and 11.11 area % of chloroform were detected, and production of 26.18 area % of dichlorocyclopropane derivative was confirmed in a high retention time region.

Example 6

Operations were carried out in the same way as in Example 1 with the exception that, in Example 1, 6.6 g of potassium hydroxide was changed to 4.0 g of sodium hydroxide and the amount of water was changed from 4.6 g to 4.0 g. When stirring was stopped, the contents were allowed to settle, and the organic layer was analyzed by gas chromatography, 0.90 area % of 1-butene, 1.73 area % of (E)-2-butene, 1.16 area % of (Z)-2-butene, 63.42 area % of 2-fluorobutane, and 12.97 area % of chloroform were detected, and production of 19.63 area % of dichlorocyclopropane derivative was confirmed in a high retention time region.

Example 7

Operations were carried out in the same way as in Example 1 with the exception that, in Example 1, the amount of water was changed from 4.6 g to 2.3 g. When stirring was stopped, the contents were allowed to settle, and the organic layer was analyzed by gas chromatography, 1.01 area % of 1-butene, 2.12 area % of (E)-2-butene, 1.41 area % of (Z)-2-butene, 63.36 area % of 2-fluorobutane, and 12.10 area % of chloroform were detected, and production of 19.81 area % of dichlorocyclopropane derivative was confirmed in a high retention time region.

Example 8

Operations were carried out in the same way as in Example 1 with the exception that, in Example 1, 6.6 g of potassium hydroxide was changed to 16.8 g of cesium hydroxide monohydrate and the amount of water was changed from 4.6 to 3.45 g. When stirring was stopped, the contents were allowed to settle, and the organic layer was analyzed by gas chromatography, 1.17 area % of 1-butene, 1.68 area % of (E)-2-butene, 0.95 area % of (Z)-2-butene, 60.13 area % of 2-fluorobutane, and 11.26 area % of chloroform were detected, and production of 24.62 area % of dichlorocyclopropane derivative was confirmed in a high retention time region.

Example 9

A 100 mL glass reaction vessel equipped with a stirrer and a Dimroth condenser (0° C. coolant circulated in condenser)

was charged with 6.6 g of potassium hydroxide and was cooled to 0° C. The reaction vessel was further charged with 4.6 g of water to dissolve the potassium hydroxide. Next, 10 mL of chloroform was added as trihalomethane. In addition, 10.5 g of the mixture obtained in Production Example 1 (crude 2-fluorobutane containing butenes) and 0.13 g of benzyltriethylammonium chloride as a phase transfer catalyst were added. The organic layer was analyzed by gas chromatography at this point and was found to contain 2.24 area % of 1-butene, 10.64 area % of (E)-2-butene, 9.25 area % of (Z)-2-butene, 64.75 area % of 2-fluorobutane, and 12.99 area % of chloroform. The contents of the reaction vessel were vigorously stirred for 30 minutes at 0° C. and were further stirred for 2.5 hours at 50° C. Thereafter, the stirring was stopped, the contents were allowed to settle, and the organic layer was reanalyzed by gas chromatography. In this analysis, 0.03 area % of 1-butene, 0.01 area % of (E)-2-butene, 0.01 area % of (Z)-2-butene, 62.78 area % of 2-fluorobutane, and 11.73 area % of chloroform were detected, and production of 24.57 area % of dichlorocyclopropane derivative was confirmed in a high retention time region.

Example 10

Operations were carried out in the same way as in Example 1 with the exception that, in Example 1, the amount of potassium hydroxide was changed from 6.6 g to 4.95 g and the amount of water was changed from 4.6 g to 3.45 g. When stirring was stopped, the contents were allowed to settle, and the organic layer was analyzed by gas chromatography, 0.33 area % of 1-butene, 0.32 area % of (E)-2-butene, 0.19 area % of (Z)-2-butene, 63.36 area % of 2-fluorobutane, and 12.10 area % of chloroform were detected, and production of 23.69 area % of dichlorocyclopropane derivative was confirmed in a high retention time region.

Example 11

A 100 mL glass reaction vessel equipped with a stirrer and a Dimroth condenser (0° C. coolant circulated in condenser) was charged with 6.6 g of potassium hydroxide and was cooled to 0° C. The reaction vessel was further charged with 4.6 g of water to dissolve the potassium hydroxide. Next, 10 mL of bromoform was added as trihalomethane. In addition, 10.5 g of the mixture obtained in Production Example 1 (crude 2-fluorobutane containing butenes) and 0.13 g of benzyltriethylammonium chloride as a phase transfer catalyst were added. The organic layer was analyzed by gas chromatography at this point and was found to contain 2.02 area % of 1-butene, 10.19 area % of (E)-2-butene, 8.96 area % of (Z)-2-butene, 62.14 area % of 2-fluorobutane, and 16.67 area % of bromoform. The contents of the reaction vessel were vigorously stirred for 30 minutes at 0° C. and were further stirred for 8 hours at room temperature. Thereafter, the stirring was stopped, the contents were allowed to settle, and the organic layer was reanalyzed by gas chromatography. In this analysis, 0.79 area % of 1-butene, 1.27 area % of (E)-2-butene, 0.82 area % of (Z)-2-butene, 67.54 area % of 2-fluorobutane, and 9.99 area % of bromoform were detected, and production of 15.33 area % of dibromocyclopropane derivative was confirmed in a high retention time region.

Example 12

A 100 mL glass reaction vessel equipped with a stirrer and a Dimroth condenser (0° C. coolant circulated in condenser) was charged with 6.6 g of potassium hydroxide and was cooled to 0° C. The reaction vessel was further charged with 4.6 g of water to dissolve the potassium hydroxide. Next, 10 mL of bromodichloromethane was added as trihalomethane. In addition, 10.4 g of the mixture obtained in Production Example 1 (crude 2-fluorobutane containing butenes) and 0.13 g of benzyltriethylammonium chloride as a phase transfer catalyst were added. The organic layer was analyzed by gas chromatography at this point and was found to contain 2.56 area % of 1-butene, 12.54 area % of (E)-2-butene, 11.08 area % of (Z)-2-butene, 64.00 area % of 2-fluorobutane, and 9.78 area % of bromodichloromethane.

The contents of the reaction vessel were vigorously stirred for 30 minutes at 0° C. and were further stirred for 8 hours at room temperature. Thereafter, the stirring was stopped, the contents were allowed to settle, and the organic layer was reanalyzed by gas chromatography. In this analysis, 0.24 area % of 1-butene, 0.52 area % of (E)-2-butene, 0.39 area % of (Z)-2-butene, 46.98 area % of 2-fluorobutane, and 7.88 area % of bromodichloromethane were detected, and production of 34.78 area %, in total, of dichlorocyclopropane derivative and bromochlorocyclopropane derivative was confirmed in a high retention time region.

Example 13

A 100 mL glass reaction vessel equipped with a stirrer and a Dimroth condenser (0° C. coolant circulated in condenser) was charged with 6.6 g of potassium hydroxide and was cooled to 0° C. The reaction vessel was further charged with 4.6 g of water to dissolve the potassium hydroxide. Next, 10 mL of chloroform was added as trihalomethane. In addition, 10.4 g of the mixture obtained in Production Example 2 (crude 2-fluorobutane containing butenes) and 0.13 g of benzyltriethylammonium chloride as a phase transfer catalyst were added. The organic layer was analyzed by gas chromatography at this point and was found to contain 2.49 area % of 1-butene, 12.31 area % of (E)-2-butene, 10.75 area % of (Z)-2-butene, 40.46 area % of 2-fluorobutane, and 33.96 area % of chloroform.

The contents of the reaction vessel were vigorously stirred for 30 minutes at 0° C. and were further stirred for 7.5 hours at room temperature. Thereafter, the stirring was stopped, the contents were allowed to settle, and the organic layer was reanalyzed by gas chromatography. In this analysis, 1.48 area % of 1-butene, 0.67 area % of (E)-2-butene, 0.26 area % of (Z)-2-butene, 47.70 area % of 2-fluorobutane, and 6.90 area % of chloroform were detected, and production of 42.81 area % of dichlorocyclopropane derivative was confirmed in a high retention time region.

Example 14

Purification of 2-Fluorobutane by Distillation

A 1 L glass reaction vessel equipped with a stirrer and a Dimroth condenser (0° C. coolant circulated in condenser) was charged with 99 g of potassium hydroxide and was cooled to 0° C. The reaction vessel was further charged with 70 g of water to dissolve the potassium hydroxide. Next, 150 mL of chloroform was added as trihalomethane. In addition, 150 g of a mixture obtained through repetition of the operations in Production Example 1 (crude 2-fluorobutane containing butenes) and 1.8 g of benzyltriethylammonium chloride as a phase transfer catalyst were added. The organic layer was analyzed by gas chromatography at this point and was found to contain 2.22 area % of 1-butene, 10.54 area % of (E)-2-butene, 9.36 area % of (Z)-2-butene, 64.45 area % of 2-fluorobutane, and 12.91 area % of chloroform.

The contents of the reaction vessel were vigorously stirred for 30 minutes at 0° C. and were further stirred for 12 hours at room temperature. Thereafter, the stirring was stopped, the contents were allowed to settle, and the organic layer was reanalyzed by gas chromatography. In this analysis, 0.91 area % of 1-butene, 0.11 area % of (E)-2-butene, 0.09 area % of (Z)-2-butene, 60.85 area % of 2-fluorobutane, and 9.31 area % of chloroform were detected, and production of 28.46 area % of dichlorocyclopropane derivative was confirmed in a high retention time region.

Next, 100 mL of water was added into the reaction vessel to dissolve a produced inorganic salt. After settling, the aqueous layer present as a lower layer was separated and the organic layer present as an upper layer was transferred to a distillation still. Distillation was carried out using a KS rectifying column (produced by Toka Seiki Co., Ltd.; column length: 60 cm; packing: Heli Pack No. 1). A coolant (−10° C.) was circulated in a condenser and total reflux was performed for approximately 1 hour. The still was heated from 65° C. to 85° C. while paying attention to the column top temperature and the remaining amount of material inside the still. After implementation of total reflux, fraction withdrawal was performed at a reflux ratio of 30:1. Approximately 3 hours after the start of extraction, a 2-fluorobutane fraction of 99.9 area % or more was obtained. As a result, 79 g of 99.97 area % 2-fluorobutane was obtained.

Example 15

A 100 mL glass reaction vessel equipped with a stirrer and a Dimroth condenser (−10° C. coolant circulated in condenser) was charged with 3.3 g of potassium hydroxide (purity: 85%) and was cooled to 0° C. The reaction vessel was further charged with 2.3 g of water to dissolve the potassium hydroxide. Next, 10 mL of chloroform was added as trihalomethane. In addition, 10.3 g of the mixture obtained in Production Example 3 (crude isobutyl fluoride containing isobutene) and 0.11 g of benzyltriethylammonium chloride as a phase transfer catalyst were added. The organic layer was analyzed by gas chromatography at this point and was found to contain 14.10 area % of isobutene, 68.13 area % of isobutyl fluoride, and 17.54 area % of chloroform.

The contents of the reaction vessel were vigorously stirred for 30 minutes at 0° C. and were further stirred for 8 hours at room temperature. Thereafter, the stirring was stopped, the contents were allowed to settle, and the organic layer was reanalyzed by gas chromatography. In this analysis, 1.82 area % of isobutene, 70.30 area % of isobutyl fluoride, and 13.84 area % of chloroform were detected, and production of 13.73 area % of dichlorocyclopropane derivative was confirmed in a high retention time region.

Example 16

Operations were carried out in the same way as in Example 15 with the exception that, in Example 15, 3.3 g of potassium hydroxide was changed to 2 g of sodium hydroxide and the amount of water was changed from 2.3 g to 2.0 g. When stirring was stopped, the contents were allowed to settle, and the organic layer was analyzed by gas chromatography, 3.10 area % of isobutene, 72.39 area % of isobutyl fluoride, and 13.44 area % of chloroform were detected, and production of 10.76 area % of dichlorocyclopropane derivative was confirmed in a high retention time region.

Comparative Example 1

Distillation of 129 g of a mixture obtained by repeating the operations in Production Example 1 (mixture containing 2.82 area % of 1-butene, 12.33 area % of (E)-2-butene, 10.81 area % of (Z)-2-butene, and 72.45 area % of 2-fluorobutane) was performed using the same distillation column as used in Example 14. A coolant (−10° C.) was circulated in the condenser, and total reflux was performed for approximately 1 hour. The still was heated from 40° C. to 50° C. while paying attention to the column top temperature and the remaining amount of material inside the still. Fraction withdrawal was performed at a reflux ratio of 45:1 to 30:1. As a result, the time taken to remove the butenes and reach a fraction purity of 99.0 area % or more was 9 hours. Finally, 45 g of 99.12 area % 2-fluorobutane was obtained.

The results of this distillation demonstrate that removal of butenes from crude 2-fluorobutane having high butene content is time consuming and is industrially problematic in terms of production efficiency.

Comparative Example 2

A 100 mL glass reaction vessel equipped with a gas introduction tube and a stirrer was charged with 30 mL of 1,1,2-trifluorotrichloroethane, was immersed in a dry ice/ethanol bath, and was cooled to −70° C. Next, 20 g of the mixture obtained in Production Example 1 (crude 2-fluorobutane) was added into the reaction vessel, and 10.7 g of chlorine gas was introduced into the reaction vessel over 1 hour from the gas introduction tube, via a mass flow controller. A further 30 minutes of stirring was performed at −70° C. When the contents of the reaction vessel were subsequently analyzed by gas chromatography, 2.21 area % of 1-butene, 3.41 area % of (E)-2-butene, and 3.09 area % of (Z)-2-butene were found to be remaining, and 13.4 area % of a chlorinated compound of 2-fluorobutane was detected.

The results of Examples 1 to 16 and Comparative Examples 1 and 2 are summarized below in Table 1.

Note that in Table 1, with regard to the trihalomethane, chloroform is indicated as 2A, bromoform is indicated as 2B, and bromodichloromethane is indicated as 2C, and with regard to the alkali aqueous solution, 85% potassium hydroxide is indicated as 3A, sodium hydroxide is indicated as 3B, and cesium hydroxide monohydrate is indicated as 3C.

Moreover, with regard to the phase transfer catalyst, benzyltriethylammonium chloride is indicated as 4A, tetrabutylammonium sulfate is indicated as 4B, tetrabutylammonium bromide is indicated as 4C, tetraphenylphosphonium bromide is indicated as 4D, and tetrabutylphosphonium bromide is indicated as 4E.

Note that in Examples 1 to 14 and Comparative Examples 1 and 2, the monofluorobutane is 2-fluorobutane, whereas in Examples 15 and 16, the monofluorobutane is isobutyl fluoride.

TABLE 1

| | (1) Crude monofluorobutane (g) | (2) Trihalomethane (mL) | (3) Alkali aqueous solution (alkali metal hydroxide/water) (g/g) | (4) Phase transfer catalyst (g) | Pre-conversion (area %) | | | |
|---|---|---|---|---|---|---|---|---|
| | | | | | Monofluorobutane | \ Butenes \ 1-Butene | E-2-butene | Z-2-butene |
| Example 1 | 10.1 | 2A: 10 | 3A: 6.6/4.6 | 4A: 0.13 | 73.71 | 2.71 | 12.61 | 10.97 |
| Example 2 | 10.1 | 2A: 10 | 3A: 6.6/4.6 | 4B: 0.34 | 73.71 | 2.71 | 12.61 | 10.97 |
| Example 3 | 10.1 | 2A: 10 | 3A: 6.6/4.6 | 4C: 0.19 | 73.71 | 2.71 | 12.61 | 10.97 |
| Example 4 | 10.1 | 2A: 10 | 3A: 6.6/4.6 | 4D: 0.21 | 73.71 | 2.71 | 12.61 | 10.97 |
| Example 5 | 10.1 | 2A: 10 | 3A: 6.6/4.6 | 4E: 0.17 | 73.71 | 2.71 | 12.61 | 10.97 |
| Example 6 | 10.1 | 2A: 10 | 3B: 4.0/4.0 | 4A: 0.13 | 73.71 | 2.71 | 12.61 | 10.97 |
| Example 7 | 10.1 | 2A: 10 | 3A: 6.6/2.3 | 4A: 0.13 | 73.71 | 2.71 | 12.61 | 10.97 |
| Example 8 | 10.1 | 2A: 10 | 3C: 16.8/3.45 | 4A: 0.13 | 73.71 | 2.71 | 12.61 | 10.97 |
| Example 9 | 10.5 | 2A: 10 | 3A: 6.6/4.6 | 4A: 0.13 | 73.71 | 2.71 | 12.61 | 10.97 |
| Example 10 | 10.1 | 2A: 10 | 3A: 4.95/3.45 | 4A: 0.13 | 73.71 | 2.71 | 12.61 | 10.97 |
| Example 11 | 10.5 | 2B: 10 | 3A: 6.6/4.6 | 4A: 0.13 | 73.71 | 2.71 | 12.61 | 10.97 |
| Example 12 | 10.4 | 2C: 10 | 3A: 6.6/4.6 | 4A: 0.13 | 73.71 | 2.71 | 12.61 | 10.97 |
| Example 13 | 10.4 | 2A: 10 | 3A: 6.6/4.6 | 4A: 0.13 | 58.84 | 4.13 | 19.80 | 17.23 |
| Example 14 | 150 | 2A: 150 | 3A: 99/70 | 4A: 1.8 | 73.71 | 2.71 | 12.61 | 10.97 |
| Example 15 | 10.3 | 2A: 10 | 3A: 3.3/2.3 | 4A: 0.11 | 85.36 | Isobutene: 14.02 | | |
| Example 16 | 10.3 | 2A: 10 | 3B: 2.0/2.0 | 4A: 0.11 | 85.36 | Isobutene: 14.02 | | |
| Comparative Example 1 | 129 | 9 hours of distillation | | | 72.45 | 2.82 | 12.33 | 10.81 |
| Comparative Example 2 | 20 | Introduction of chlorine gas | | | 73.71 | 2.71 | 12.61 | 10.97 |

| | Post-conversion (area %) | | | | | |
|---|---|---|---|---|---|---|
| | Monofluorobutane | Butenes | | | Trihalomethane | High-boiling point compound |
| | | 1-Butene | E-2-butene | Z-2-butene | | |
| Example 1 | 61.25 | 0.95 | 0.15 | 0.04 | 8.00 | 29.54 |
| Example 2 | 64.55 | 1.30 | 3.62 | 2.59 | 13.01 | 14.71 |
| Example 3 | 66.46 | 1.18 | 3.68 | 2.75 | 12.72 | 13.09 |
| Example 4 | 58.40 | 0.90 | 1.27 | 0.83 | 12.86 | 25.61 |
| Example 5 | 60.03 | 1.08 | 0.90 | 0.50 | 11.11 | 26.18 |
| Example 6 | 63.42 | 0.90 | 1.73 | 1.16 | 12.97 | 19.63 |
| Example 7 | 63.36 | 1.01 | 2.12 | 1.41 | 12.10 | 19.81 |
| Example 8 | 60.13 | 1.17 | 1.68 | 0.95 | 11.26 | 24.62 |
| Example 9 | 62.78 | 0.03 | 0.01 | 0.01 | 11.73 | 24.57 |
| Example 10 | 63.36 | 0.33 | 0.32 | 0.19 | 12.10 | 23.69 |
| Example 11 | 67.54 | 0.79 | 1.27 | 0.82 | 9.99 | 15.33 |
| Example 12 | 46.98 | 0.24 | 0.52 | 0.39 | 7.88 | 34.78 |
| Example 13 | 47.70 | 1.48 | 0.67 | 0.26 | 6.90 | 42.81 |
| Example 14 | 60.85 | 0.91 | 0.11 | 0.09 | 9.31 | 28.46 |
| Example 15 | 70.30 | Isobutene: 1.82 | | | 13.84 | 13.73 |
| Example 16 | 72.39 | Isobutene: 3.10 | | | 13.44 | 10.76 |
| Comparative Example 1 | 99.12 | | | | — | — |
| Comparative Example 2 | Chlorinated product: 13.40 | 2.21 | 3.41 | 3.09 | — | — |

It can be seen from Table 1 that the majority of the butene(s) could be removed in a simple manner by conversion treatment in Examples 1 to 16.

Moreover, the target was obtained with a purity of 99.97 area % or more from the reaction liquid obtained in Example 14 through a 3-hour distillation operation.

On the other hand, it can be seen that when butenes were removed only by distillation without conversion treatment in Comparative Example 1, the distillation was time consuming, productivity was poor, and purity of the obtained 2-fluorobutane was low, which is industrially disadvantageous.

Moreover, when removal of butenes using chlorine gas was attempted in Comparative Example 2, although reduction of the butene content was achieved, 2-fluorobutane was chlorinated, leading to loss of the target 2-fluorobutane.

The invention claimed is:

1. A monofluorobutane purification method comprising:
    bringing crude monofluorobutane containing butene into contact with trihalomethane in the presence of an alkali aqueous solution to convert the butene to a compound having a higher boiling point than the monofluorobutane,
    subsequently adding water to a reaction mixture obtained thereby to dissolve a produced salt,
    separating an organic layer, and
    purifying by distillation the organic layer that is separated.

2. The monofluorobutane purification method according to claim 1, wherein the crude monofluorobutane contains the butene in a proportion of at least 5 mass % and not more than 50 mass %.

3. The monofluorobutane purification method according to claim 1, wherein the contact is performed in the presence of a phase transfer catalyst.

4. The monofluorobutane purification method according to claim 1, wherein the alkali aqueous solution is an aqueous solution of an alkali metal hydroxide.

* * * * *